United States Patent [19]

Reich et al.

[11] Patent Number: 5,602,191
[45] Date of Patent: Feb. 11, 1997

[54] PREPARATION OF RADIATION-CURABLE ACRYLATES THAT ARE STORAGE STABLE WITH ISOCYANATE CROSSLINKING AGENTS

[75] Inventors: Wolfgang Reich, Maxdorf; Erich Beck, Schriesheim; Edmund Keil, Heuchelheim; Ulrich Erhardt, Ladenburg; Adolf Nuber, Iggelheim, all of Germany

[73] Assignee: BASF Aktiengesellschaft, Ludwigshafen, Germany

[21] Appl. No.: 455,621

[22] Filed: May 31, 1995

[30] Foreign Application Priority Data

Jun. 8, 1994 [DE] Germany ............ 44 20 012.9

[51] Int. Cl.⁶ ................................. C08F 2/46
[52] U.S. Cl. ............... 522/174; 522/25; 522/28; 522/30; 522/64; 522/65
[58] Field of Search ............ 522/174, 31, 64, 522/65, 25, 28, 30

[56] References Cited

U.S. PATENT DOCUMENTS

| | | |
|---|---|---|
| 3,432,478 | 3/1969 | May . |
| 3,833,384 | 9/1974 | Noonan et al. . |
| 4,205,018 | 5/1980 | Nagasawa et al. ............ 522/103 |
| 5,096,938 | 3/1992 | Beck et al. ............ 522/100 |

FOREIGN PATENT DOCUMENTS

| | | |
|---|---|---|
| 657091 | 6/1965 | Belgium . |
| 0054105 | 6/1982 | European Pat. Off. . |
| 0279303 | 8/1988 | European Pat. Off. . |
| 3316593A1 | 11/1984 | Germany . |

*Primary Examiner*—Mark Chapman
*Attorney, Agent, or Firm*—Oblon, Spivak, McClelland, Maier & Neustadt, P.C.

[57] ABSTRACT

Radiation-curable acrylates are prepared by a process in which the hydroxy compound is reacted with acrylic acid or methacrylic acid in a first stage and, in a second stage, the reaction product of the first stage is reacted with an epoxide compound in the presence of, as a catalyst, a quaternary ammonium or phosphonium compound of the general formula

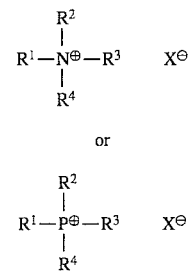

where $X^{\ominus}$ is an opposite ion and $R^1$ to $R^4$ independently of one another are each $C_1$–$C_{18}$-alkyl which may be substituted by one or two phenyl groups or are each $C_6$–$C_{12}$-aryl which may be substituted by one or two $C_1$–$C_6$-alkyl groups.

8 Claims, No Drawings

PREPARATION OF RADIATION-CURABLE ACRYLATES THAT ARE STORAGE STABLE WITH ISOCYANATE CROSSLINKING AGENTS

The present invention relates to a process for the preparation of radiation-curable acrylates. EP-A-54 105, DE-A-33 16 593 and EP-A-279 303 disclose processes in which a (meth)acrylate is prepared from (meth)acrylic acid and a hydroxy compound in a first stage and excess (meth)acrylic acid is reacted with epoxides in a second stage. DE-A-33 16 593 mentions tertiary amines or Lewis bases, such as thiodiglycol as catalysts for the reaction in the second stage. In EP-A-54 105, triphenylphosphine is used as a catalyst. In EP-A-279 303, quaternary ammonium compounds are also mentioned in addition to tertiary amines and Lewis bases in general form.

The radiation-curable acrylates prepared by the known processes have some disadvantages. Thus, with the addition of isocyanate crosslinking agents, for example to increase the hardness of coatings, radiation-curable formulations having an insufficient shelf life, ie. insufficient time for processing before the beginning of crosslinking, are obtained. Furthermore, undesirable settling out of components of the resulting radiation-curable formulation is observed when, for example, fillers or pigments are added to the radiation-curable acrylates known to date.

It is an object of the present invention to provide a process for the preparation of radiation-curable acrylates which does not have these disadvantages.

We have found that this object is achieved by a process which comprises reacting a hydroxy compound with acrylic acid or methacrylic acid in a first stage and, in a second stage, reacting the reaction product of the first stage with an epoxide compound in the presence of, as a catalyst, a quaternary ammonium or phosphonium compound of the general formula

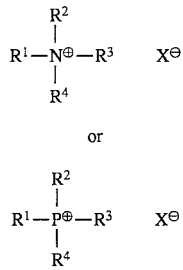

where $X^\ominus$ is an opposite ion and $R^1$ to $R^4$ independently of one another are each $C_1$–$C_{18}$-alkyl which may be substituted by one or two phenyl groups or are each $C_1$–$C_6$-aryl which may be substituted by one or two $C_1$–$C_6$-alkyl groups.

We have also found the acrylates obtainable by this process and radiation-curable formulations which contain these acrylates.

In the novel process, acrylic acid or methacrylic acid (referred to together as (meth)acrylic acid) is reacted with a hydroxy compound. Suitable hydroxy compounds are those compounds having one or more hydroxyl groups. Examples are monoalcohols, $C_2$–$C_8$-alkylenediols, trimethylolpropane, glycerol or pentaerythritol or, for example, hydroxyl-containing compounds alkoxylated with ethylene oxide or with propylene oxide.

Preferred hydroxy compounds are saturated polyesters which contain at least 2, in particular from 2 to 6, free hydroxyl groups and may also contain ether groups, or polyethers having at least 2, in particular from 2 to 6, free hydroxyl groups.

The molecular weights $M_n$ of the polyesters or polyethers are preferably from 100 to 4000 ($M_n$ determined by gel permeation chromatography).

Such hydroxyl-containing polyesters can be prepared, for example, in a conventional manner by esterification of dicarboxylic acids or polycarboxylic acids with diols or polyols. The starting materials for such hydroxyl-containing polyesters are known to a person skilled in the art. Dicarboxylic acids which may be preferably used are succinic acid, glutaric acid, adipic acid, sebacic acid, o-phthalic acid, their isomers and hydrogenation products and esterifiable derivatives, such as anhydrides, eg. maleic anhydride, or dialkyl esters of the stated acids. An example of a suitable polycarboxylic acid is trimellitic acid. Preferred diols are ethylene glycol, 1,2- and 1,3-propylene glycol, 1,4-butanediol, 1,6-hexanediol, neopentylglycol, cyclohexanedimethanol and polyglycols of the ethylene glycol and propylene glycol type.

Examples of polyols are primarily trimethylolpropane, glycerol and pentaerythritol.

Other suitable diols or polyols are diols or polyols which are oxyalkylated (for example with ethylene oxide or propylene oxide), in particular those having a degree of oxyalkylation of from 0 to 10, based on the particular hydroxyl groups of the diol or polyol.

The polyesterols which may be used according to the invention include polycaprolactonediols and -triols, whose preparation is likewise known to a person skilled in the art.

Examples of suitable hydroxyl-containing polyethers are those which can be obtained by known processes, by reacting dihydric and/or polyhydric alcohols with various amounts of ethylene oxide and/or propylene oxide. In the case of the ethylene glycol/ propylene glycol cocondensates, the reaction can advantageously be controlled so that predominantly primary hydroxyl groups are formed as terminal groups. Polymerization products of tetrahydrofuran or butylene oxide may also be used.

Oxyalkylation products of the abovementioned diols or polyols, in particular having a degree of oxyalkylation of from 0 to 10, particularly preferably from 1 to 10, based on the particular hydroxyl groups of the diol or polyol, are preferred, but at least 2 alkoxy groups are present altogether in the polyether.

In the esterification of the (meth)acrylic acid in the case of the hydroxyl-containing polyester, it is also possible, for example, initially to take the (meth)acrylic acid together with starting materials of the hydroxyl-containing polyester, for example dicarboxylic acids or anhydrides thereof and diols or polyols, and to react the starting materials together with the (meth)acrylic acid in one stage.

In the esterification of (meth)acrylic acid with the hydroxy compound, preferably from 0.1 to 1.5, particularly preferably from 0.5 to 1.4, very particularly preferably from 0.7 to 1.3, equivalents, based on 1 hydroxyl equivalent of the hydroxy compounds, of (meth)acrylic acid are used. In the abovementioned case where starting materials of, for example, the hydroxyl-containing polyester are also present in the esterification, the number of equivalents of (meth)acrylic acid is based on the hydroxyl equivalent theoretically remaining after reaction of the starting materials, for example reaction of dicarboxylic acids with diols or polyols.

The reaction of the (meth)acrylic acid with the hydroxy compounds can be carried out, for example, in the presence of an acidic esterification catalyst, such as sulfuric acid or p-toluenesulfonic acid, and in the presence of a hydrocarbon which forms an azeotropic mixture with water, in particular to a conversion of in particular at least 85%, preferably from 90 to 95%, of the hydroxyl groups of the hydroxy compound, for example at from 60° C. to 140° C. The water of reaction formed is removed azeotropically. Suitable hydrocarbons are aliphatic and aromatic hydrocarbons, for example alkanes and cycloalkanes, such as n-hexane, n-heptane and cyclohexane, aromatics, such as benzene, toluene and xylene isomers, and special gasolines which have boiling limits of from 70° C. to 140° C.

In order to avoid premature polymerization, the reaction with (meth)acrylic acid is advantageously carried out in the presence of small amounts of inhibitors. These are the usual compounds used for preventing thermal polymerization, for example of the type comprising hydroquinone, hydroquinone monoalkyl ethers, 2,6-di-tert-butylphenol, N-nitrosamines of phenothiazines or phosphorous esters. They are generally used in amounts from 0,001 to 2.0%, preferably from 0,005 to 0.5%, based on the reaction in the first stage.

After the esterification, the solvent, for example the hydrocarbon, can be removed from the reaction mixture by distillation, if necessary under reduced pressure. The esterification catalyst can be neutralized in a suitable manner, for example by adding tertiary amines or alkali metal hydroxides.

In the second stage, the reaction product obtained in the first stage is reacted with an epoxide compound. The epoxide compounds are those having at least one epoxy group in the molecule, preferably at least two, particularly preferably two or three, epoxy groups in the molecule.

For example, epoxidized olefins, glycidyl esters of saturated or unsaturated carboxylic acids or glycidyl ethers of aliphatic or aromatic polyols are suitable. Such products are commercially available in large numbers. Polyglycidyl compounds of the bisphenol A type and glycidyl ethers of polyhydric alcohols, for example of butanediol, of glycerol and of pentaerythritol, are particularly preferred. Examples of such polyepoxide compounds are ®Epikote 812 (epoxide value: about 0.67), Epikote 828 (epoxide value: about 0.53) and Epikote 162 (epoxide value: about 0.61) from Shell.

The epoxide compounds are added to the reaction product obtained in the first stage, in general in amounts of from 1 to 20, particularly preferably from 5 to 15%, by weight, based on the reaction product of the first stage. The epoxide compounds are very particularly preferably used in about equimolar amounts, based on the acid equivalents still present in the reaction product of the first stage.

In the reaction with epoxide compounds in the second stage, acid which was used in excess or has not reacted, in particular (meth)acrylic acid, as well as, for example, dicarboxylic acid still present as starting material in the mixture, or resulting half-esters of dicarboxylic acids having a remaining acid group, are bound as epoxide esters.

The reaction with epoxide compounds is carried out preferably at from 90° to 130° C., particularly preferably from 100° to 110° C., and is preferably continued until the reaction mixture has an acid number of less than 10, particularly preferably less than 5 mg KOH/g.

Quaternary ammonium or phosphonium compounds of the general formula

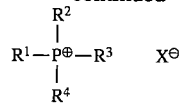

or

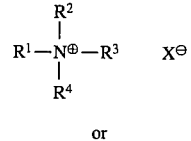

where $X^\ominus$ is an opposite ion and $R^1$ to $R^4$ independently of one another are each $C_1$–$C_{18}$-alkyl which may be substituted by one or two phenyl groups or are each $C_6$–$C_{12}$-aryl which may be substituted by one or two $C_6$–$C_{12}$-alkyl groups, are used as catalysts for the reaction of the epoxide compounds with the acid groups in the second stage. Examples of opposite ions $X^\ominus$, are $Br^\ominus$, $Cl^\ominus$, $I^\ominus$, $HSO_4^\ominus$, $OH^\ominus$, $ClO_4^\ominus$, $BF_4^\ominus$ and acetate.

$R^1$ to $R^4$ are in particular each $C_1$–$C_8$-alkyl, preferably $C_1$–$C_4$-alkyl, or benzyl.

$R^1$ to $R^4$ may be partly aliphatic and partly aromatic; in particular, one of the radicals may be aromatic while the other three radicals are aliphatic.

Particularly preferably, all radicals $R^1$ to $R^4$ are aliphatic.

In particular, phosphonium compounds of the formula II are used.

The quaternary ammonium or phosphonium compounds are preferably used in amounts of from 0.01 to 5, particularly preferably from 0.1 to 2, % by weight, based on the epoxide compounds.

The radiation-curable acrylates obtainable by the novel process are particularly suitable for use as materials which can be cured thermally, but preferably by high-energy radiation.

They may be used as or in coating materials, for example finishes, printing inks or adhesives, as printing plates, moldings, for the production of photoresists, in stereolithography or as casting materials, for example optical lenses.

For use as or in radiation-curable materials, additives, such as crosslinking agents, thickeners, leveling agents or fillers or pigments, etc., may be added to the radiation-curable acrylates (referred to below as radiation-curable formulation).

Particularly suitable crosslinking agents for subsequent crosslinking are isocyanate compounds. Suitable isocyanate compounds have at least 2 isocyanate groups.

Suitable curing agents are polyisocyanates having an average isocyanate functionality of at least 2.0, preferably from 2.2 to 5.0, and an isocyanate content of from 5 to 30, preferably from 10 to 25, % by weight and preferably a maximum viscosity of 10,000 mPa.s at 25° C. Aliphatic, cycloaliphatic and aromatic diisocyanates, eg. butane-1,4-diisocyanate, hexane-1,6-diisocyanate, 2,2,4- and 2,4,4-trimethylhexamethylene diisocyanate, cyclohexane diisocyanate, methylcyclohexane diisocyanate, isophorone diisocyanate, 4,4-diisocyanatodiphenylmethane, 4,4-diisocyanatodicy-clohexylmethane, toluylene 2,4- and 2,6-diisocyanate and tetramethylxylylene diisoxyanate, are in principle suitable. Isocyanates or biurets of the abovementioned diisocyanates are also particularly suitable.

For example, surface coating polyisocyanates, as described, for example, in European Patent 0,358,979, may also be used. These compounds are, for example, uretdione-, biuret- and isocyanurate-containing adducts of, for example, the above diisocyanates, such as 1,6-diisocyanatohexane or isophorone diisocyanate, which may have a lower viscosity of, for example, from 50 to 500 or from 50 to 3000 mPa.s at 25° C. Isocyanate curing agents which additionally contain an emulsifier in an amount which ensures dispersibility in water are particularly preferred, and the emulsifier may be a reaction product of a polyisocyanate with a monohydric or polyhydric, nonionic polyether alcohol having at least one polyether chain containing at least 10 ethylene oxide units.

Such water-emulsifiable polyisocyanates are described, for example, in European Patent 0,206,059 or German Laid-Open Application DOS 4,036,927.

The amount of the isocyanate compounds as crosslinking agents is preferably from 0.05 to 30, particularly preferably from 0.5 to 20, % by weight, based on the radiation-curable acrylates.

Radiation-curable formulations which contain the novel acrylates and isocyanate compounds have a substantially improved shelf life compared with corresponding prior art formulations, which is evident from the smaller increase in the viscosity during storage.

Examples of suitable pigments and fillers which may be added to the radiation-curable acrylates or radiation-curable formulations of the radiation-curable acrylates are inorganic or organic pigments and fillers, such as rutile, anatase, chalk, talc and $BaSO_4$.

The total amount of pigments or fillers is in general from 0 to 70, preferably from 1 to 50, % by weight, based on the radiation-curable acrylates.

Radiation-curable formulations of the novel acrylate compounds which contain pigments or fillers also have an improved shelf life, which is evident from the scarcely observable settling out of components of the formulation.

The radiation-curable acrylates or their formulations can be cured thermally, preferably by high-energy radiation, such as UV light or electron beams.

Photoinitiators are usually added for radiation-curing by means of UV light.

Suitable photoinitiators are, for example, benzophenone and derivatives thereof, such as alkylbenzophenones, halomethylated benzophenones and Michler's ketone, and benzoin and benzoin ethers, such as ethylbenzoin ether, benzil ketals, such as benzil dimethyl ketal, acetophenone derivatives, eg. hydroxy-2-methyl-1-phenylproan-1-one and hydroxycyclohexyl phenyl ketone, anthraquinone and its derivatives, such as methylanthraquinone, and in particular acrylphosphine oxides, such as Lucirin® TPO (2,4,6-trimethylbenzoyldiphenylphosphine oxide).

The photoinitiators, which, depending on the intended use of the novel materials, are employed in amounts from 0.1 to 15, preferably from 1 to 10, % by weight, based on the polymerizable components, can be used as individual substances or, owing to frequent advantageous synergistic effects, also in combination with one another.

EXAMPLE a) Preparation of the Polyester Acrylate

In a 2 l apparatus, 694.6 g of ethoxylated trimethylolpropane having an OH number of 630 mg KOH/g, 190 g of adipic acid, 327.3 g of methylcyclohexane, 424.5 g of acrylic acid and 6.5 g of concentrated sulfuric acid are heated in the presence of suitable stabilizers. 156 g of water are separated off in the course of 6.5 hours. The methylcyclohexane and excess acrylic acid are then removed under reduced pressure to an acid number (AN) of 42.6 mg KOH/g of substance.

The batch is divided up as follows:
18.3 g of tetrabutylammonium bromide (NBu4Br) and 70.6 g of bisphenol A diglycidyl ether are added to 500 g of crude ester at from 106° to 108° C. After a reaction time of 7 hours, the product is filtered and filled.

| AN: | 0.2 mg KOH/g of substance |
| --- | --- |
| Iodine color number (ICN): | 3 to 4 |
| Viscosity: | 3.1 Pa · s |

Note:
$NBu_4Br$ is a better catalyst than tributylamine, so that smaller amounts of catalyst and, owing to the lower level of secondary reactions, also less epoxide would be required.

2. 10.5 g of tributylamine (equimolar) and 70.6 g of bisphenol A diglycidyl ether are added to 500 g of crude ester at from 106° to 108° C. After a reaction time of 7 hours, the product is filtered and filled.

| Final AN: | 3.9 mg KOH/g of substance |
| --- | --- |
| ICN: | 5 to 7 |
| Viscosity: | 2.9 Pa · s | b) Compatibility With Isocyanates 5 parts of a polyisocyanate (Basonat® P LR 8781) are added to 100 parts of each of the polyacrylates from 1. and 2., and the mixture is stored at 60° C. and the appearance and increase in viscosity are observed.

The resin from batch 2. had completely gelled after only 14 hours. The resin from batch 1. had a viscosity of 5.8 Pa.s after 105 hours.

We claim:

1. A process for the preparation of a storage stable composition comprising a radiation-curable acrylate and an isocyanate crosslinking agent, which comprises reacting a hydroxy compound with acrylic acid or methacrylic acid in a first stage and, in a second stage, reacting the reaction product of the first stage with an epoxide compound in the presence of, as a catalyst, a quaternary ammonium or phosphonium compound of the formula

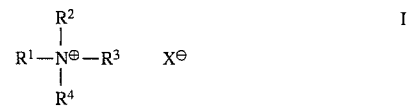

or

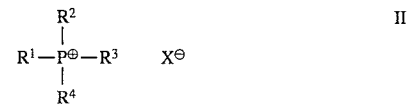

where $X^{\ominus}$ is an opposite ion and $R^1$ to $R^4$ independently of one another are each $C_1$–$C_{18}$-alkyl which may be substituted by one or two phenyl groups or are each $C_6$–$C_{12}$-aryl which may be substituted by one or two $C_1$–$C_6$-alkyl groups, to form a radiation-curable acrylate, and then adding thereto an isocyanate crosslinking agent.

2. A process as claimed in claim 1, wherein $R^1$ to $R^4$ independently of one another are each $C_1$–$C_8$-alkyl.

3. A process as claimed in claim 1, wherein a phosphonium compound of the formula II is added as a catalyst.

4. A process as claimed in claim 1, wherein the hydroxy compound is a saturated polyester which contains at least two hydroxyl groups in the molecule and may also contain ether groups, or is a polyether containing at least two hydroxyl groups in the molecule.

5. A process as claimed in claim 1, wherein the epoxide compound is a diepoxide compound or triepoxide compound.

6. A storage stable composition obtainable by a process as claimed in claim 1.

7. A storage stable composition as claimed in claim 6 wherein the isocyanate crosslinking agent contains at least two isocyanate groups.

8. A storage stable composition as claimed in claim 7, containing from 0.05 to 30% by weight, based on the radiation-curable acrylate, of the isocyanate compound.

\* \* \* \* \*